US005424787A

United States Patent [19]
Zegarelli

[11] Patent Number: 5,424,787
[45] Date of Patent: Jun. 13, 1995

[54] EYEGLASSES WITH MASK SUPPORT ATTACHMENT MEANS

[76] Inventor: Peter J. Zegarelli, 592 Bedford Rd., Pocantico Hills, N.Y. 10591

[21] Appl. No.: 262,852

[22] Filed: Jun. 20, 1994

[51] Int. Cl.⁶ .............................................. G02C 5/14
[52] U.S. Cl. ............................. 351/111; 351/158; 2/429
[58] Field of Search ............... 351/111, 123, 155, 158, 351/41; 2/13, 429, 444, 448, 173, 206

[56] References Cited

U.S. PATENT DOCUMENTS

| | | | |
|---|---|---|---|
| 1,279,884 | 9/1918 | Roche | 2/206 |
| 2,900,639 | 10/1955 | Lindstrom | 2/13 |
| 3,266,111 | 12/1961 | Abel | 351/111 |
| 4,843,643 | 7/1989 | Parissenti et al. | 2/13 |

FOREIGN PATENT DOCUMENTS 0232072  8/1959  Australia ............................ 2/206

Primary Examiner—William L. Sikes
Assistant Examiner—Huy Mai
Attorney, Agent, or Firm—James J. Romano, Jr.

[57] ABSTRACT

A pair of eyeglasses is provided and comprises attachment pieces formed on the temple pieces anterior of the eyeglasses ear pieces for the attachment of the non-rigid support ties of a non-rigid face mask thereto to support the face mask from the eyeglasses temple pieces rather than the ears of the wearer. The combination of the pair of eyeglasses and the thusly supported mask is also provided. The pair of eyeglasses may take the form of safety glasses, and the mask the form of a conventional surgical mask.

10 Claims, 3 Drawing Sheets

EYEGLASSES WITH MASK SUPPORT ATTACHMENT MEANS

BACKGROUND OF THE INVENTION

1. Field of the Invention

This invention relates to new and improved eyeglasses comprising attachment means on the eyeglass temple pieces for the practical, readily removable attachment of the non-rigid support means of non-rigid face masks, for example conventional surgical masks or the like, to the eyeglasses to support the mask therefrom, thus removing the stress of mask support from the ears of the wearer; and to the combination of the eyeglasses and the thusly attached and supported mask.

2. Description of the Prior Art

Although the support of face masks from eyeglasses is known in the prior art, the same will generally be seen to be directed to the support of essentially rigid, impervious face masks taking, for example, the form of plastic face shields or the like, wherein the mean for attaching the mask to the eyeglasses are included in the face mask support means, which are normally of essentially rigid, somewhat mechanically complex and bulky configuration, rather than being formed on the eyeglasses independently of the mask support means; it having been determined in accordance with the teachings of my invention that the inclusion in the non-rigid support means of conventional surgical masks, which generally take the form of simple elastic ties, of attachment means to practically and readily removable attach the same to a pair of eyeglasses to support the mask therefrom, rather than to loop the elastic mask support ties around the ears of the wearer to support the mask therefrom in conventional manner, would be extremely difficult and, in any event, would add materially to the cost of the surgical mask which is of course disposable.

With more specific regard to the prior art, U.S. Pat. No. 4,944,039 to Dietrich discloses the attachment of the rigid support means of a rigid impervious plastic mask 112 to the temple pieces 200 of a pair of eyeglasses 202 by hooks or spring clips 103 which are included as parts of the mask support means and which extend over the eyeglass temple pieces 200 to attach and support the mask 112 therefrom; it being immediately clear to those skilled in this art that the hooks 103 are not formed on the eyeglass temple pieces, and that the mask 112 is by no means a conventional surgical mask.

U.S. Pat. No. 3,991,753 to Viesca y Viesca discloses the attachment of the rigid support means of a rigid impervious plastic mask sheet 10 to the lens frame 28 of a pair of spectacles 26 by rigid mounting clips 20 which are screwed to the mask sheet 10 and extend over the lens frame 28 to attach and support the mask sheet 10 from the spectacles 26; it again being immediately clear that mounting clips 20 are not formed on the eyeglass temple pieces, and that the mask sheet 10 is by no means a conventional surgical mask.

U.S. Pat. No. 4,821,340 to Johnson discloses the attachment and support of an essentially impervious, except for vent holes 18, rigid plastic mask sheet or face shield 11 from a pair of eyeglasses 31 through use of a rigid clip portion 13 which is snap fitted into the mask shield 11 and extends over the bridge portion 34 of the lens frame of the eyeglasses 31 to attach and support the mask sheet 11 therefrom. Replacement of the mask sheet 11 is apparently made possible by removal of the clip portion 13 from the eyeglasses 31, the removal of the mask shield 11 therefrom and the replacement of the same by a new mask shield; although this is made somewhat unclear by the statement at lines 8 and 9 of column 3 of the Johnson specification that "The clip portion 13 is a permanent part of the face shield 10 . . . " Clip portion 13 is not, in any event, formed as part of the eyeglasses 31, and is not located on the temple pieces thereof; while mask sheet 11 is again not a conventional surgical mask.

U.S. Pat. No. 4,945,573 to Landis discloses the attachment of the essentially rigid visor support means 16 for a rigid, impervious plastic mask shield 26 to the temple pieces 11 of a pair of eyeglasses 12 by the extension of the temple pieces through slits 24 in the visor 16 to support the mask shield 26 from the eyeglasses. Clearly, the slits 24 in the visor 16 are not included in the eyeglass temple pieces 11, and the mask shield 26 is not a conventional surgical mask.

U.S. Pat. No. 4,965,887 to Paoluccio discloses the attachment and support of a rigid, impervious plastic clear lens shield 1 and net-like head cover from the temple pieces of a pair of eyeglasses 6 by spring loaded clips 2 which are fixedly secured to the lens shield 1 by double coated, pressure sensitive high tack adhesive tape 3. Again, the spring loaded clips 2 are clearly not included in the eyeglass temple pieces, and the lens shield 1 is not a conventional surgical mask.

U.S. Pat. No. 2,023,523 to Grimball discloses the formation of closed eyelets Tb or open eyelets Tc on the rear ends of the temple pieces T—T of a pair of eyeglasses for the attachment of hooks b of an elastic band B, or a simple elastic band B', respectively, thereto to prevent the eyeglasses from falling from the head of the wearer. Clearly, neither of the closed eyelets Tb, or the open eyelets Tc which open forwardly relative to the eyeglass frame F, would be effective as a practical matter to attach the closed elastic ties of a conventional surgical mask to the Grimball eyeglasses for the support of the mask therefrom; and this observation would apply with equal force to all of the face mask or shield attachment/support means as disclosed by the other patents of the prior art as discussed in some detail directly hereinabove.

OBJECTS OF THE INVENTION

It is, accordingly, an object of my invention to provide new and improved eyeglasses comprising attachment means for the practical, readily removable attachment of the non-rigid support means of non-rigid face masks, for example conventional surgical masks or the like, to support the masks therefrom, thereby removing the stress of mask support from the ears of the wearer.

It is another object of my invention to provide eyeglasses as above wherein the attachment means are of particularly simple and virtually foolproof configuration and manner of operation, and comprise no moving parts, thereby assuring the reliability thereof, and a useful attachment means life equal to that of the eyeglasses.

It is another object of my invention to provide eyeglasses comprising attachment means as above which enable the immediate and convenient removal of the mask from the attachment means and replacement of the same by a new mask without in any way affecting or requiring adjustment of any nature or replacement of the attachment means.

It is another object of my invention to provide eyeglasses as above wherein the same are safety glasses and, as such, particularly adapted for use in accordance with contemporary OSHA requirements by health care providers in the nature, for example, of dentists and surgeons and nurses who are also now required to wear surgical masks.

It is another object of my invention to provide eyeglasses comprising attachment means as above which are disposed on the respective eyeglass temple pieces as close as practical to the anterior portions of the ears of the wearer to thus insure disposition of a surgical mask as supported therefrom relative to the face of the wearer in manner equally effective in all material respects to that provided by support of the surgical mask in heretofore conventional manner from the ears of the wearer.

It is another object of my invention to provide eyeglasses comprising attachment means as above which enable the wearer of the eyeglasses to very conveniently remove one of the mask support means from one of the attachment means on one of the eyeglass temple pieces to displace the mask from the face of the wearer to allow unrestricted conversation with a patient intermediate a procedure or the performance of other tasks with which the mask might interfere while nonetheless retaining the other mask support means securely attached to the eyeglasses for the convenient reattachment of the mask to the eyeglasses for the continuance of the procedure.

It is another object of my invention to provide eyeglasses comprising attachment means as above wherein the attachment means are totally independent of and form no part of the mask, which is normally disposable, and which thus add nothing to the complexity or cost of the mask.

It is another object of my invention to provide eyeglasses comprising attachment means as above wherein the attachment means may be formed integrally with the eyeglass temple pieces, or very readily and simply secured thereto to, in any event, add very little to the cost of the eyeglasses.

It is a further object of my invention to provide a new and improved combination of the eyeglasses and mask as above.

SUMMARY OF THE INVENTION

As representatively disclosed herein the currently contemplated best mode of my invention comprises a pair of safety glasses which include a lens frame, temple pieces extending respectively from opposite sides of said lens frame, ear pieces extending respectively from said temple pieces, and attachment means on the temple pieces for the attachment of the elastic non-rigid support ties of a surgical mask to the temple pieces to support the surgical mask therefrom, thereby relieving the ears of the wearer of the safety glasses and surgical mask from the aggravation and stress of the unrelenting tension of the elastic mask support ties as would normally be looped therearound to support the surgical mask on the face of the wearer. The attachment means comprise generally L-shaped attachment pieces which are respectively disposed on the temple pieces at substantially corresponding locations thereon immediately anterior of the ear pieces, and which cooperate with the temple pieces to form attachment grooves into which the looped elastic surgical mask support ties can be stretched and disposed to support the mask from the pair of safety glasses. The invention also comprises the combination of the pair of safety glasses and the thusly supported surgical mask. The configuration and manner of operation of the attachment grooves vis-a-vis those of the non-rigid surgical mask support ties render immediately practical and convenient the removal of one, only, of the support ties from one of the attachment grooves to free the face of the wearer from the surgical mask for activities with which the same might interfere while nonetheless leaving the surgical mask securely attached to and supported from the pair of safety glasses from the other of the support ties in the other of the attachment grooves, and immediately available for reattachment as described to again cover the face of the wearer. Although representatively disclosed as applicable for use by medical personnel in the nature of dentists, surgeons or nurses, the pair of safety glasses and the combination thereof with the supported surgical mask of the invention should find equal use applicability by a wide range of non-medical personnel in the nature, for example, of industrial workers.

DESCRIPTION OF THE DRAWINGS

The above and other significant objects and advantages of my invention are believed made clear by the following derailed description thereof taken in conjunction with the accompanying drawings wherein:

FIG. 6 is a perspective view of the safety glasses-surgical mask combination of FIG. 4 more fully depicting the operative disposition thereof on the ears, nose and mouth of the wearer.

DETAILED DESCRIPTION OF THE INVENTION

Prior to detailed description of my invention, it is to be understood that the independent support of both a pair of eyeglasses and a surgical mask in heretofore conventional manner from the ears of a health care provider, for example a dentist or surgeon or nurse who are now in any event required by applicable OSHA regulations to wear safety glasses and a surgical mask attendant the performance of dental and/or surgical procedures, has been determined to be sufficiently stressful, especially after long periods or intermittent periods of long overall duration of wear, to go well beyond simple irritation or pain to the ears and actually result in headaches, primarily as a result of the stress imposed upon the ears of the health care provider as above by the unrelenting tension of the elastic mask ties which are stretched and looped over the ears of the wearer to retain the mask in place over the wearer's nose and mouth. In addition, it may be understood that the temporary removal of the surgical mask intermittent a procedure by the dentist or surgeon to, for example, allow unrestricted conversation with the patient or other attending medical personnel, or to perform other tasks such as checking support equipment or test results or simply to take a drink of water, generally requires that the mask ties be removed from both ears to completely remove the mask from any semblance of support from the ears of the wearer, and the subsequent repositioning of the mask ties around the ears of the wearer to continue the procedure; it having been determined that efforts to leave the mask supported by only one elastic mask support tie to hang loosely from one ear of the wearer are at best unwieldly and, in many instances, by no means totally satisfactory.

Further, removal of one or both of the mask ties from one or both ears of the wearer as above oftentimes result in the displacement of the safety glasses earpiece(s) from one or both ears of the wearer, as the case may be, due to entanglement of the support tie with the earpiece in each instance; and this of course proves extremely inconvenient during any dental or surgical procedure.

Figure 1:
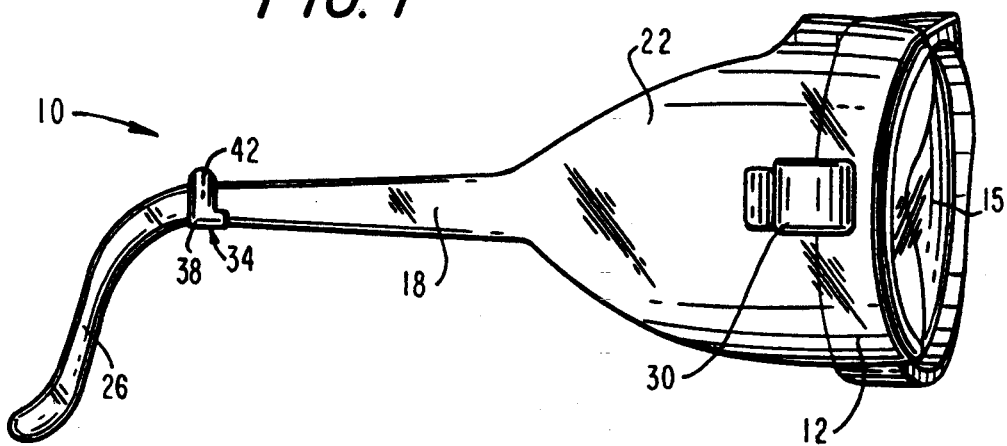
FIG. 1 is a side view of a pair of safety glasses representatively configured and operable in accordance with the currently contemplated best mode of my invention.
Figure 2:
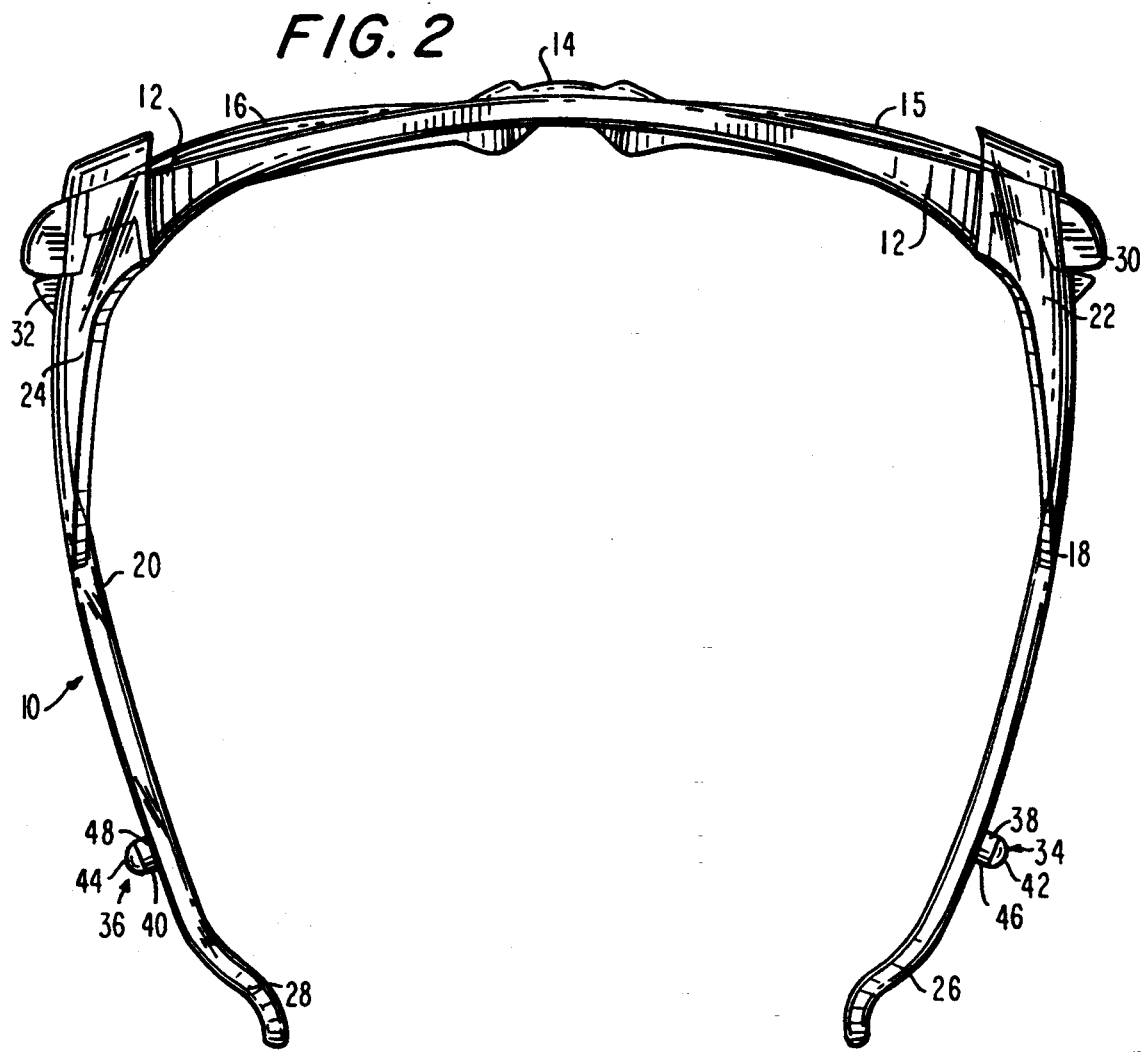
FIG. 2 is a top view of the pair of safety glasses of FIG. 1.
Figure 3:
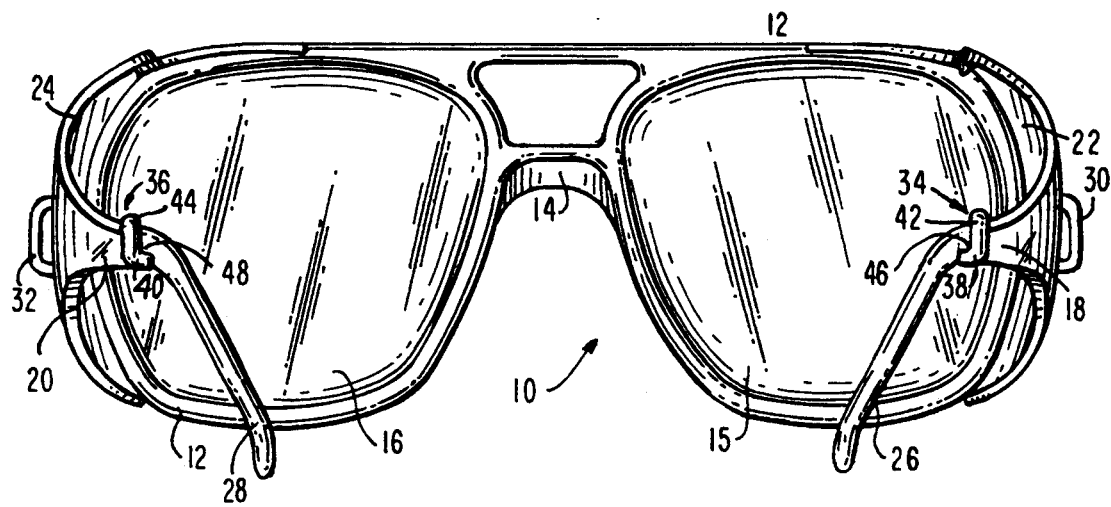
FIG. 3 is a rear view of the pair of safety glasses of FIG. 1.

With the above in mind, and referring now to FIGS. 1, 2 and 3 of the application drawings, a pair of representative transparent safety glasses made, for example, of a suitable plastic, is indicated generally at 10; and, in conventional manner, comprises a lens frame 12 including a bridge portion 14 for the support of the safety glasses from the nose of the wearer, lenses 15 and 16 operatively disposed in the openings provided therefor in the lens frame 12, fight and left temple frames or pieces as indicated at 18 and 20 and respectively including enlarged eye-protective side portions 22 and 24, and terminating at the respective outer end portions thereof in downwardly curved ear pieces as indicated at 26 and 28 for extension over the ears of the wearer to support the safety glasses 10 therefrom. Hinges as indicated at 30 and 32 are respectively formed as shown at the junctures of the lens frame 12 and the inner end portions of the fight and left temple pieces 18 and 20 and suitably attached thereto to pivotally connect the temple pieces 18 and 20 to the lens frame 12 and allow for the opening and closing of the pair of safety glasses 10.

Right and left mask attachment pieces as indicated generally at 34 and 36, are respectively disposed as shown at essentially corresponding locations on the right and left temple pieces 18 and 20 immediately anterior in each instance to the points at which the temple pieces commence to curve downwardly to form the ear pieces 26 and 28. As best seen in application drawing FIG. 1, 2, 3 and 5, the attachment pieces are of generally L-shaped configuration in respectively comprising base portions 38 and 40 which extend generally perpendicularly from the outer sides of the fight and left temple pieces 18 and 20, and leg portions 42 and 44 which extend upwardly from the base portions 38 and 40 generally parallel to the outer temple pieces sides to terminate above the levels of the same; thereby resulting in each instance in the formation of attachment grooves as indicated at 46 and 48 by the described combination of the respective outer side surfaces of the temple pieces 18 and 20 and the attachment pieces 34 and 36. The attachment pieces 34 and 36 may, for example, also be formed of an appropriate plastic material and, as such, formed integrally with the temple pieces 18 and 20 by injection molding. Alternatively, the attachment pieces may be fabricated separately of the temple pieces and securely affixed thereto in any convenient manner, for example by a suitable epoxy.

Figure 4:
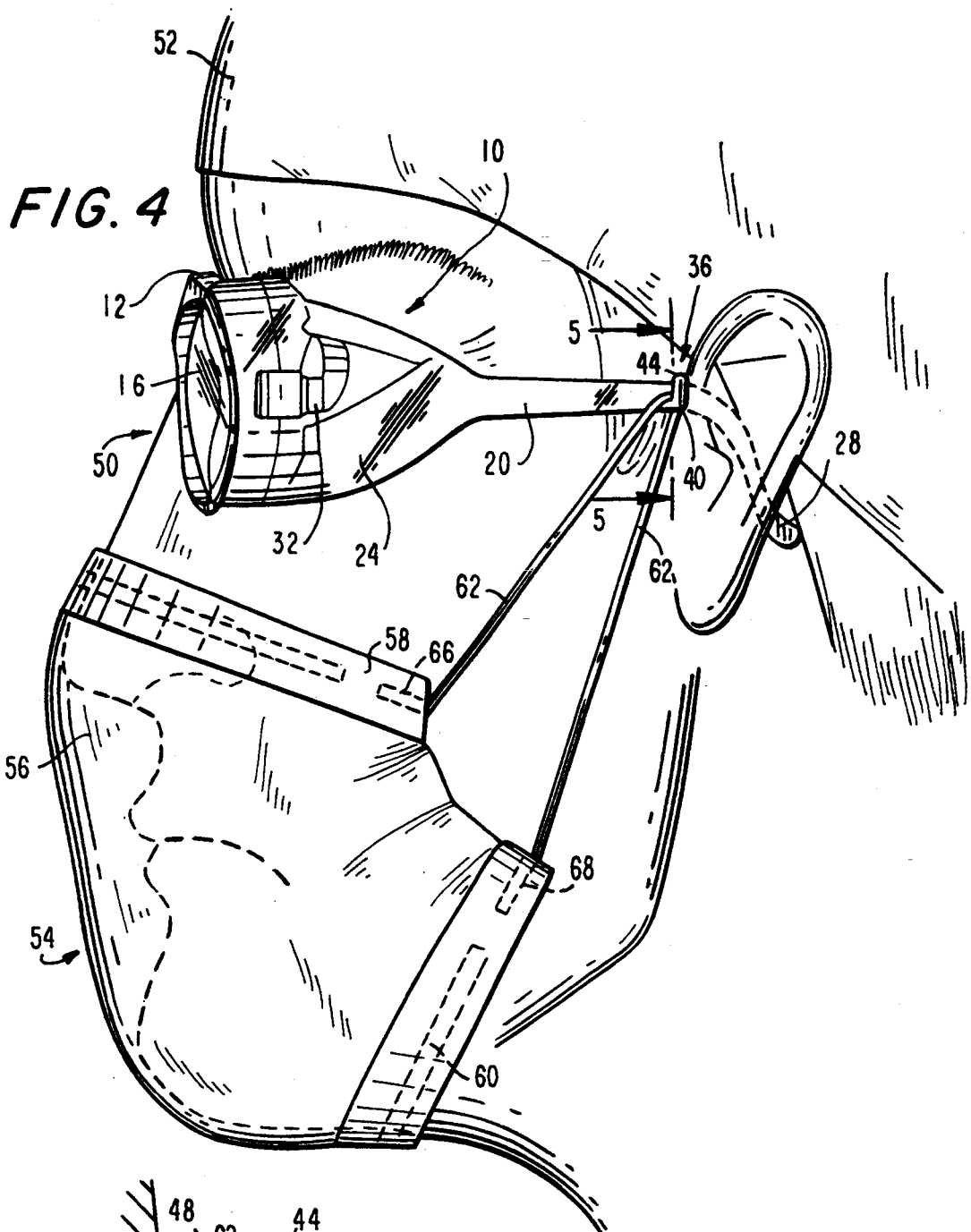
FIG. 4 is a partial side view of the pair of safety glasses of FIG. 1 operatively disposed on the ears and nose of the wearer in combination with a conventional surgical mask as attached to and supported from the safety glasses to cover the nose and mouth of the wearer.
Figure 5:
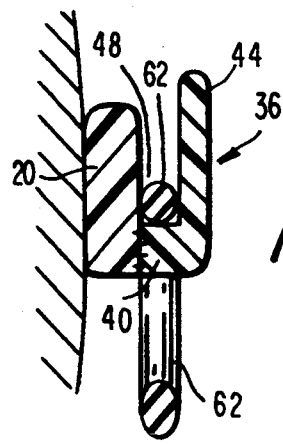
FIG. 5 is cross-sectional view taken essentially along line 5—5 in FIG. 4.

In use, and as best seen in application drawing FIGS. 4, 5 and 6, the pair of safety glasses 10 are operatively disposed in conventional manner on the ears and nose of the head of the wearer as indicated generally at 50, and depicted for purposes of representative illustration of the teachings of my invention as a dentist or surgeon to include a conventional medical hair cap 52.

A conventional, non-rigid surgical mask is indicated generally at 54 in application drawing FIGS. 4 and 6, and comprises a mask body portion 56 of an appropriately porous gauze material, with mask pore size being determined to be effective to prevent the passage through the mask of patient-originated viral and/or bacterial matter for ingestion into the nose and mouth of the wearer of the mask 54. For use, for example, by a dentist in the performance of a dental procedure requiring the use of by now conventional, air/water turbine powered extremely high speed dental drills, a major purpose of the mask 54 would be to prevent the ingestion of the resultant aerosol-borne infected particulate matter from the teeth of the patient by the dentist.

Further included in the surgical mask 54 are suitably reinforced, folded over upper and lower mask edge portions as indicated at 58 and 60, respectively; and non-rigid, elastic mask support ties 62 and 64 which are securely affixed to the upper and lower reinforced mask edge portions 58 and 60 at opposite sides thereof as indicated at 66 and 68 for mask support tie 62, and 70 and 72 for mask support tie 64. This of course results in the formation as shown of closed mask support loops by the respective mask support ties 62 and 64.

Attachment of the surgical mask 54 to the pair of safety glasses 10 to support the mask therefrom on the head 50 of the wearer and cover the wearer's nose and mouth is readily and conveniently accomplished as illustrated by FIGS. 4 and 6 of the application drawings by the simple stretching and placement of the elastic mask support ties 62 and 64 in the attachment grooves 46 and 48 formed as heretofore described by the attachment piece 34 and temple piece 18 of the safety glasses 10, and by the attachment piece 36 and temple piece 20 of the safety glasses 10, respectively; with application drawing FIG. 5 representatively illustrating the snug and secure fit of the looped mask support tie 62 in the attachment groove 48 of the safety glasses 10.

With the surgical mask 54 attached to and supported from the pair of safety glasses 10 on the head of the wearer to cover the wearer's nose and mouth as shown and described, it will be immediately clear to those skilled in this art that the ears of the wearer will be totally relieved of the aggravation and stress of the unrelenting tension of the stretched elastic mask support ties 62 and 64, with that unrelenting tension having been directly transferred to the safety glasses 10; it having been determined that the very slight weight or pull now added to the safety glasses 10 by the thusly attached and supported, extremely light surgical mask 54, as now of course applied instead to both the nose and ears of the wearer by the lens frame bridge portion 14 and the downwardly curved ear pieces 26 and 28 of the safety glasses 10, is totally non-aggravating or stressful and is, in fact, so slight as to be virtually unnoticeable even after prolonged periods of wear of the safety glasses-surgical mask combination of my invention.

In addition to the significant advantages provided by the teachings of my invention as set forth hereinabove, it may be understood that the same further provide for the temporary removal of the surgical mask 54 to uncover the face of the wearer while nonetheless leaving the mask conveniently and securely supported from the pair of safety glasses 10 on the head 50 of the wearer for convenient and immediate re-attachment of the mask to the safety glasses to again cover the face of the wearer as depicted in application drawing FIGS. 4 and 6. More specifically, and although not shown, it will be immediately clear to those skilled in this art that, by virtue of the configuration and manner of operation of the attachment pieces 34 and 36 vis-a-vis those of the elastic mask support ties 62 and 64, the removal of one of those support ties, for example mask tie 64, from the attachment groove 46 formed as heretofore described by the attachment piece 34 on glasses temple piece 18, will be effective to enable the surgical mask to simply swing over to the left under the force of gravity and uncover the face of the wearer, with the mask nonetheless remaining conveniently and securely supported from the pair of safety glasses 10 on the head of the wearer by the attachment of the mask support tie 62 in the attachment groove 48 formed by the attachment piece 36 on the left mask temple piece 20 as depicted in application drawing FIG. 5. This enables the wearer of the surgical mask 54 to freely converse with the patient or other medical personnel who may be on the scene, and/or to perform any other task not requiring the face to be covered by the mask and with which the mask would interfere, without the mask hanging loosely in somewhat bothersome and not always fully satisfactory manner from one ear, as is now the practice; and provides for the immediate and convenient re-covering of the face of the wearer by the surgical mask 54 for continuance of the medical procedure at hand by the simple grasping of the mask support tie 64 and stretching thereof to re-position the same in the mask attachment groove 46 formed by attachment piece 34 on the right temple piece 18 of the safety glasses 10.

In like manner, adjustment of the safety glasses-supported surgical mask 54 relative to the face of the wearer, for example to tighten the mask, is rendered particularly convenient by the attachment pieces 34 and 36 of my invention in requiring only the grasping of the lower or inner runs of the mask support ties 62 and 64 and the downward pulling thereon to slide the support ties through the attachment grooves 46 and 48 to the extent required to tighten the mask 54 about the face to the desired degree; it being immediately clear to those skilled in this art that this manner of tightening the mask relative to the face of the wearer is infinitely less aggravating and stressful to the ears of the wearer than it would be with the mask supported in heretofore conventional manner from the wearer's ears, and particularly if repeated adjustments of the tightness of the mask prove necessary, as for example during an extended dental or surgical procedure wherein the mask may be repeatedly detached from one of the attachment grooves 46 or 48 to uncover the face of the wearer and subsequently re-attached thereto as described in detail hereinabove.

Although representatively disclosed herein in accordance with the currently contemplated best mode of my invention as directed to the attachment and support of a surgical mask from a pair of safety glasses as worn by medical practitioners in the nature of dentists or surgeons, it is to be understood that the new and improved eyeglasses, and combination thereof with a protective face mask, of my invention are also applicable to equally advantageous utilization by a wide variety of non-medical personnel, for example industrial workers or the like, in the performance of endeavors wherein the wearing of safety glasses and a non-rigid protective face mask in the nature, for example, of a painting or sanding mask or the like is mandated either by law or by the simple dictates of common sense.

Various changes may of course be made in my invention as disclosed herein without departing from the spirit and scope thereof as defined in the appended claims.

What is claimed is:

1. In a pair of eyeglasses which comprise a lens frame, temple pieces extending respectively from opposite sides of said lens frame, and ear pieces extending respectively from said temple pieces, the improvements comprising, attachment means on said temple pieces for attaching the non-rigid support ties of a surgical mask thereto for the support of said surgical mask from said temple pieces, said attachment means comprising attachment pieces respectively formed on said temple pieces and independent of said surgical mask support ties.

2. In a pair of eyeglasses as in claim 1, the improvements further comprising, said attachment pieces being formed on said temple pieces anterior of said ear pieces.

3. In a pair of eyeglasses as in claim 1, the improvements further comprising, said attachment pieces being operable to form attachment grooves on said temple pieces for the disposition of said surgical mask support ties therein to support said surgical mask from said temple pieces, whereby said support ties may be readily removed from said attachment grooves to unattach the same from said temple pieces and enable the ready removal of said surgical mask from said eyeglasses.

4. In a pair of eyeglasses as in claim 1, the improvements further comprising, said pair of eyeglasses being a pair of safety glasses.

5. In a pair of eyeglasses as in claim 2, the improvements further comprising, said attachment pieces being formed at substantially corresponding locations on said temple pieces relative to said ear pieces.

6. In combination, a pair of eyeglasses comprising a lens frame, temple pieces extending respectively from opposite sides of said lens frame, and ear pieces extending respectively from said temple pieces, a surgical mask comprising non-rigid support ties, attachment means on said temple frames for attaching the non-rigid support ties of said surgical mask thereto for the support of said surgical mask from said temple pieces, said attachment means comprising attachment pieces respectively disposed on said temple pieces and independent of said surgical mask support ties.

7. The combination of claim 6 wherein, said attachment pieces are disposed on said temple frames anterior of said ear pieces.

8. The combination of claim 6 wherein, said support ties extend from opposite sides of said surgical mask, said attachment pieces being operable to form attachment grooves on said temple, pieces for the disposition being operable to form of said surgical mask support ties therein to support said surgical mask from said temple pieces, whereby one of said support ties may be readily removed from one of said attachment grooves to nonetheless leave said surgical mask supported from said eyeglasses by the other of said support ties in the other of said attachment grooves.

9. The combination of claim 6 wherein, said pair of eyeglasses comprise a pair of safety glasses.

10. The combination of claim 6 wherein, said attachment pieces are disposed at substantially corresponding locations on said temple pieces relative to said ear pieces.

* * * * *